(12) United States Patent
McCrea et al.

(10) Patent No.: US 10,639,413 B2
(45) Date of Patent: May 5, 2020

(54) BLOOD FILTRATION SYSTEM CONTAINING MANNOSE COATED SUBSTRATE

(71) Applicant: ExThera Medical Corporation, Martinez, CA (US)

(72) Inventors: Keith McCrea, Concord, CA (US); Robert Ward, Lafayette, CA (US); Olle Larm, Bromma (SE); Lars Adolfsson, Uppsala (SE)

(73) Assignee: Exthera Medical Corporation, Martinez, CA (US)

( * ) Notice: Subject to any disclaimer, the term of this patent is extended or adjusted under 35 U.S.C. 154(b) by 0 days.

(21) Appl. No.: 16/053,272

(22) Filed: Aug. 2, 2018

(65) Prior Publication Data

US 2019/0038826 A1     Feb. 7, 2019

Related U.S. Application Data

(60) Division of application No. 14/973,617, filed on Dec. 17, 2015, now abandoned, which is a continuation of
(Continued)

(51) Int. Cl.
*A61M 1/34* (2006.01)
*A61M 1/36* (2006.01)
(Continued)

(52) U.S. Cl.
CPC ............. *A61M 1/34* (2013.01); *A61M 1/36* (2013.01); *A61M 1/3679* (2013.01);
(Continued)

(58) Field of Classification Search
CPC .... A61M 1/34; A61M 1/3679; A61M 1/3687; A61M 2205/7518; A61M 2202/203;
(Continued)

(56) References Cited

U.S. PATENT DOCUMENTS

| 3,782,382 A | 1/1974 | Naftulin et al. |
|---|---|---|
| 4,103,685 A | 8/1978 | Lupien et al. |

(Continued)

FOREIGN PATENT DOCUMENTS

| CN | 101370536 A | 2/2009 |
|---|---|---|
| CN | 102740859 A | 10/2012 |

(Continued)

OTHER PUBLICATIONS

Abdul-Razzak, K. et al., "Fetal and newborn calf thymus as a source of chromatin proteins: Purification of HMG-1 and HMG-2," Preparative Biochemistry and Biotechnology, 17(1):51-61, 1987.
(Continued)

*Primary Examiner* — Pamela H Weiss
(74) *Attorney, Agent, or Firm* — Kilpatrick Townsend & Stockton LLP

(57) ABSTRACT

A blood filtration method, system, device and media for removing gram negative bacteria from the blood wherein the media includes a substrate coated with mannose optionally in constitution with substrate coated with heparin.

12 Claims, 2 Drawing Sheets

Related U.S. Application Data application No. PCT/US2014/043358, filed on Jun. 20, 2014.

(60) Provisional application No. 61/838,854, filed on Jun. 24, 2013.

(51) Int. Cl.
| | | |
|---|---|---|
| *C07H 1/00* | (2006.01) | |
| *B01D 71/08* | (2006.01) | |
| *B01D 65/08* | (2006.01) | |
| *B01D 63/10* | (2006.01) | |
| *B01D 63/08* | (2006.01) | |
| *B01D 39/04* | (2006.01) | |
| *B01D 39/08* | (2006.01) | |
| *B01D 39/16* | (2006.01) | |

(52) U.S. Cl.
CPC .......... *A61M 1/3687* (2013.01); *B01D 39/04* (2013.01); *B01D 39/083* (2013.01); *B01D 39/1615* (2013.01); *B01D 63/08* (2013.01); *B01D 63/10* (2013.01); *B01D 65/08* (2013.01); *B01D 71/08* (2013.01); *C07H 1/00* (2013.01); *A61M 1/3673* (2014.02); *A61M 2202/203* (2013.01); *A61M 2205/33* (2013.01); *A61M 2205/3334* (2013.01); *A61M 2205/7518* (2013.01)

(58) Field of Classification Search
CPC .. A61M 1/3673; A61M 1/36; A61M 2205/33; A61M 2205/3334; B01D 71/08; B01D 63/08; B01D 65/08; B01D 63/10; B01D 39/083; B01D 39/1615; B01D 39/04; C07H 1/00
See application file for complete search history.

(56) References Cited

U.S. PATENT DOCUMENTS

| | | | |
|---|---|---|---|
| 4,415,665 A | 11/1983 | Mosbach et al. | |
| 4,430,496 A | 2/1984 | Abbott | |
| 4,613,665 A | 9/1986 | Larm | |
| 4,637,994 A | 1/1987 | Tani et al. | |
| 4,820,302 A | 4/1989 | Woodroof | |
| 4,955,870 A | 9/1990 | Ridderheim et al. | |
| 5,116,962 A | 5/1992 | Stuber et al. | |
| 5,211,850 A | 5/1993 | Shettigar et al. | |
| 5,403,917 A | 4/1995 | Boos et al. | |
| 5,437,861 A | 8/1995 | Okarma et al. | |
| 5,447,859 A | 9/1995 | Prussak | |
| 5,476,509 A | 12/1995 | Keogh, Jr. et al. | |
| 5,753,227 A | 5/1998 | Strahilevitz | |
| 6,037,458 A | 3/2000 | Hirai et al. | |
| 6,159,377 A | 12/2000 | Davankov et al. | |
| 6,197,568 B1 | 3/2001 | Marks et al. | |
| 6,248,127 B1 | 6/2001 | Shah et al. | |
| 6,312,907 B1 | 11/2001 | Guo et al. | |
| 6,461,665 B1 | 10/2002 | Scholander | |
| 6,544,727 B1 | 4/2003 | Hei | |
| 6,559,290 B1 | 5/2003 | Nakatani et al. | |
| 6,653,457 B1 | 11/2003 | Larm et al. | |
| 7,179,660 B1 * | 2/2007 | Kirakossian ......... G01N 33/548 428/403 |
| 7,408,045 B2 | 8/2008 | Maruyama et al. | |
| 7,695,609 B2 | 4/2010 | Soundarrajan et al. | |
| 8,663,148 B2 | 3/2014 | Larm et al. | |
| 8,758,286 B2 | 6/2014 | Ward et al. | |
| 9,173,989 B2 | 11/2015 | Larm et al. | |
| 9,408,962 B2 | 8/2016 | Ward et al. | |
| 9,669,150 B2 | 6/2017 | Larm et al. | |
| 9,764,077 B2 | 9/2017 | Larm et al. | |
| 10,086,126 B2 | 10/2018 | Ward et al. | |
| 10,188,783 B2 | 1/2019 | Larm et al. | |
| 10,457,974 B2 | 10/2019 | Ward et al. | |
| 10,487,350 B2 | 11/2019 | Ward et al. | |
| 2001/0005487 A1 | 6/2001 | Kamibayashi et al. | |
| 2002/0018985 A1 | 2/2002 | Eible et al. | |
| 2002/0058032 A1 | 5/2002 | Hirai et al. | |
| 2002/0068183 A1 | 6/2002 | Huang et al. | |
| 2002/0197249 A1 | 12/2002 | Brady et al. | |
| 2002/0197252 A1 | 12/2002 | Brady et al. | |
| 2003/0021780 A1 | 1/2003 | Smith et al. | |
| 2003/0044769 A1 | 3/2003 | Ogino et al. | |
| 2003/0148017 A1 | 8/2003 | Tuominen et al. | |
| 2004/0084358 A1 | 5/2004 | O'Mahony et al. | |
| 2004/0115278 A1 | 6/2004 | Putz et al. | |
| 2004/0140265 A1 | 7/2004 | Lihme | |
| 2004/0176672 A1 | 9/2004 | Silver et al. | |
| 2004/0182783 A1 | 9/2004 | Walker et al. | |
| 2004/0185553 A9 | 9/2004 | Hei | |
| 2004/0202783 A1 | 10/2004 | Baumann et al. | |
| 2005/0098500 A1 | 5/2005 | Collins et al. | |
| 2005/0142542 A1 | 6/2005 | Hei et al. | |
| 2005/0244371 A1 | 11/2005 | Lentz | |
| 2005/0271653 A1 | 12/2005 | Strahilevitz | |
| 2006/0093999 A1 | 5/2006 | Hei | |
| 2006/0252054 A1 | 11/2006 | Ping | |
| 2007/0190050 A1 | 8/2007 | Davidner et al. | |
| 2007/0218514 A1 | 9/2007 | Smith et al. | |
| 2007/0231217 A1 | 10/2007 | Clintone et al. | |
| 2008/0021365 A1 | 1/2008 | Kobayashi et al. | |
| 2008/0138434 A1 | 6/2008 | Brady et al. | |
| 2008/0268464 A1 | 10/2008 | Schumacher et al. | |
| 2008/0314817 A1 | 12/2008 | Fujita et al. | |
| 2009/0105194 A1 | 4/2009 | Flengsrud et al. | |
| 2009/0136586 A1 | 5/2009 | Larm et al. | |
| 2009/0173685 A1 | 7/2009 | Imai et al. | |
| 2009/0206038 A1 | 8/2009 | Thomas | |
| 2009/0246800 A1 | 10/2009 | Mattingly et al. | |
| 2009/0325276 A1 | 12/2009 | Battrell | |
| 2010/0069816 A1 | 3/2010 | Brady et al. | |
| 2010/0079360 A1 | 4/2010 | McLaughlin et al. | |
| 2010/0098666 A1 | 4/2010 | Wright | |
| 2010/0112725 A1 | 5/2010 | Babu et al. | |
| 2010/0145317 A1 | 6/2010 | Laster et al. | |
| 2010/0216226 A1 | 8/2010 | Hyde et al. | |
| 2010/0217173 A1 | 8/2010 | Hyde et al. | |
| 2010/0239673 A1 | 9/2010 | Linhardt | |
| 2010/0249689 A1 | 9/2010 | Larm et al. | |
| 2010/0276359 A1 | 11/2010 | Ippommatsu et al. | |
| 2010/0291588 A1 | 11/2010 | McDevitt | |
| 2010/0326916 A1 | 12/2010 | Wrazel et al. | |
| 2011/0150911 A1 | 6/2011 | Choo | |
| 2011/0171713 A1 | 7/2011 | Bluchel et al. | |
| 2011/0184377 A1 * | 7/2011 | Ward .................... A61K 31/60 604/500 |
| 2011/0224645 A1 | 9/2011 | Winqvist et al. | |
| 2012/0040429 A1 | 2/2012 | Federspiel et al. | |
| 2012/0305482 A1 | 12/2012 | McCrea et al. | |
| 2013/0102948 A1 | 4/2013 | Reich et al. | |
| 2013/0131423 A1 | 5/2013 | Wang et al. | |
| 2014/0012097 A1 | 1/2014 | McCrea et al. | |
| 2014/0131276 A1 | 5/2014 | Larm et al. | |
| 2014/0231357 A1 | 8/2014 | Ward et al. | |
| 2015/0111849 A1 | 4/2015 | McCrea et al. | |
| 2015/0260715 A1 | 9/2015 | Hu et al. | |
| 2016/0022898 A1 | 1/2016 | Larm et al. | |
| 2016/0082177 A1 | 3/2016 | Ward et al. | |
| 2016/0084835 A1 | 3/2016 | Ward et al. | |
| 2016/0101229 A1 | 4/2016 | McCrea et al. | |
| 2016/0214935 A1 | 7/2016 | Hutchinson et al. | |
| 2016/0331886 A1 | 11/2016 | Ward et al. | |
| 2017/0035956 A1 | 2/2017 | McCrea et al. | |
| 2017/0073727 A1 | 3/2017 | Ward et al. | |
| 2017/0340803 A1 | 11/2017 | Larm et al. | |
| 2018/0361050 A1 | 12/2018 | Ward et al. | |
| 2019/0143027 A1 | 5/2019 | Larm et al. | |

FOREIGN PATENT DOCUMENTS

| | | |
|---|---|---|
| DE | 4217917 A1 | 12/1993 |
| EP | 0306617 A | 3/1989 |

(56) References Cited

FOREIGN PATENT DOCUMENTS

| | | |
|---|---|---|
| EP | 0321703 A | 6/1989 |
| EP | 0533946 A1 | 3/1993 |
| EP | 0616845 A | 9/1994 |
| EP | 0810027 A | 12/1997 |
| EP | 1044696 A2 | 10/2000 |
| EP | 1057529 A | 12/2000 |
| EP | 1110602 A | 6/2001 |
| EP | 1219639 A | 7/2002 |
| EP | 2087916 A1 | 8/2009 |
| EP | 2556849 A1 | 2/2013 |
| GB | 2172812 A | 10/1986 |
| JP | 54-127493 U | 9/1979 |
| JP | 58-053757 A | 3/1983 |
| JP | 58-146354 A | 8/1983 |
| JP | 4-89500 A | 3/1992 |
| JP | 6040926 A | 2/1994 |
| JP | 6-505248 A | 6/1994 |
| JP | 7-178161 A | 7/1995 |
| JP | 96-510166 A | 10/1996 |
| JP | 11-502703 A | 3/1999 |
| JP | 2000-086688 A | 3/2000 |
| JP | 2000-217575 A | 8/2000 |
| JP | 2000-515543 A | 11/2000 |
| JP | 2001-190273 A | 7/2001 |
| JP | 2002-505101 A | 2/2002 |
| JP | 2002-509518 A | 3/2002 |
| JP | 2003-128502 A | 5/2003 |
| JP | 2003-520048 A | 7/2003 |
| JP | 2005-514127 A | 5/2005 |
| JP | 2005-519744 A | 7/2005 |
| JP | 2005-532130 A | 10/2005 |
| JP | 2009-521413 A | 6/2009 |
| JP | 2010-518046 A | 5/2010 |
| JP | 2010-530288 A | 9/2010 |
| JP | 2012-501708 A | 1/2012 |
| JP | 2013-512078 A | 4/2013 |
| JP | 2014-500735 A | 1/2014 |
| KR | 10-2008-0077405 A | 8/2008 |
| WO | 91/04086 A | 4/1991 |
| WO | 92/14361 A1 | 9/1992 |
| WO | 94/26399 A1 | 11/1994 |
| WO | 95/05400 | 2/1995 |
| WO | 96/29083 A1 | 9/1996 |
| WO | 96/40857 A1 | 12/1996 |
| WO | 97/35660 A1 | 10/1997 |
| WO | 98/05341 A1 | 2/1998 |
| WO | 98/29727 A2 | 7/1998 |
| WO | 99/06086 A1 | 2/1999 |
| WO | 99/45104 A3 | 11/1999 |
| WO | 00/23792 | 4/2000 |
| WO | 00/038763 | 7/2000 |
| WO | 00/66260 A | 11/2000 |
| WO | 01/18060 A | 3/2001 |
| WO | 01/53525 A2 | 7/2001 |
| WO | 02/060512 | 8/2002 |
| WO | 03/033143 A1 | 4/2003 |
| WO | 2003/057356 A2 | 7/2003 |
| WO | 2003/078023 A1 | 9/2003 |
| WO | 2004/008138 A2 | 1/2004 |
| WO | 2004/009798 A2 | 1/2004 |
| WO | 2005/021799 A2 | 3/2005 |
| WO | 2007/058592 A1 | 5/2007 |
| WO | 2007/069983 A1 | 6/2007 |
| WO | 2007/101064 A2 | 9/2007 |
| WO | 2007/146162 A2 | 12/2007 |
| WO | 2008/095905 A2 | 8/2008 |
| WO | 2008/157570 A2 | 12/2008 |
| WO | 2010/029317 A2 | 3/2010 |
| WO | 2011/068897 A1 | 6/2011 |
| WO | 2011/100354 A1 | 8/2011 |
| WO | 2012/051595 A1 | 4/2012 |
| WO | 2012/112724 A1 | 8/2012 |
| WO | 2012/172341 A2 | 12/2012 |
| WO | 2013/188073 A1 | 12/2013 |
| WO | 2014/209782 A1 | 12/2014 |
| WO | 2015/069942 A1 | 5/2015 |
| WO | 2015/164198 A1 | 10/2015 |

OTHER PUBLICATIONS

Alarabi, A. et al., "Treatment of pruritus in cholestatic jaundice by bilirubin- and bile acid-adsorbing resin column plasma perfusion," Scandinavian Journal of Gastroenterology; 27(3):223-6, 1992.

Alfaro et al., "Interleukin-8 in cancer pathogenesis, treatment and follow-up," Cancer Treat Rev., Nov. 2017, vol. 60:24-31 (abstract only).

Axelsson, J. et al., "Cytokines in blood from septic patients interact with surface-immobilized heparin," ASAIO Journal, 56:48-51, 2010.

Bhakdi, S. and Tranum-Jensen, J., "Alpha-toxin of *Staphylococcus aureus*," Microbiological Reviews, 55(4):733-751, 1991.

Bindslev et al., "Treatment of acute respiratory failure by extracorporeal carbon dioxide elimination performed with a surface heparinized artificial lung," Anesthesiology, 67(1):117-120, 1987.

Bjorklund et al., Abstract of "Synthesis of silica-based heparin-affinity adsorbents," J. Chrom. A:, 728(1-2):149-169, 1996.

Celik, T. et al., "Treatment of lyme neuroborreliosis with plasmapheresis," J. Clinical Apheresis, 31:476-478, 2016.

Chase, H., "Affinity separations utilising immobilised monoclonal antibodies—a new tool for the biochemical engineer," Chemical Engineering Science, 39(7-8):1099-1125, 1984.

Chen et al., "Microbial subversion of heparin sulfate proteoglycans," Mol. Cells, 26:415-426, 2008.

Dixon et al., "Anthrax," New England Journal of Medicine, 341(11):815-826, 1999.

Dubreuil et al., "Effect of heparin binding on Helicobacter pylori resistance to serum," J. Med. Micro., 53:9-12, 2004.

Francy, D. et al., "Comparison of filters for concentrating, microbial indicators and pathogens in lake water samples," Applied and Environmental Microbiology, 79(4):1342-52, 2012.

Fujita, M. et al., "Adsorption of inflammatory cytokines using a heparin-coated extracorporeal circuit," Artificial Organs, 26(12):1020-1025, 2002.

Garg, L. et al., "Isolation and separation of HMG proteins and hiStones H1 and H5 and core histones by column chromatography on phosphocellulose," Protein Expression and Purification, 14(2):155-159, 1998.

Haase et al., "The effect of three different miniaturized blood purification devices on plasma cytokine concentration in an ex vivo model of endotoxinemia," Int. J. Artif. Organs, 31(8):722-729, 2008.

Hirmo, S. et al., "Sialyglycoconjugate- and proteoglycan-binding microbial lectins," Institute of Medical Microbiology, University of Lund, (Online). Retrieved Oct. 19, 1997 (Retrieved on Mar. 16, 2004). Retrieved from the Internet: <URL: http//www.plab.ku.dk/tcbh/Lectins12/Hirmo/paper.htm>.

International Preliminary Report on Patentability, dated Aug. 21, 2013, PCT Application No. PCT/US2012/025316; 8 pages.

International Search Report; PCT/SE2006/001421 dated Mar. 30, 2007.

International Search Report; PCT/US2010/058596 dated Mar. 29, 2011.

International Search Report; PCT/US2011/024229 dated May 30, 2011.

International Search Report; PCT/US2012/025316 dated May 23, 2012.

International Search Report; PCT/US2013/042377 dated Sep. 9, 2013.

International Search Report; PCT/US2014/043358 dated Dec. 1, 2014,

International Search Report; PCT/US2014/064419 dated Feb. 12, 2015.

International Search Report; PCT/US2015/026340 dated Jul. 28, 2015.

International Search Report; PCT/US2015/051239 dated Dec. 17, 2015.

(56) References Cited

OTHER PUBLICATIONS

International Search Report; PCT/US2016/057121 dated Dec. 30, 2016.
International Search Report; PCT/US2017/058536; dated Jan. 17, 2018.
Kenig, M. et al., "Identification of the heparin-binding domain of TNF-alpha and its use for efficient TNF-alpha purification by heparin-Sepharose affinity chromatography," J. Chromatography B, 867:119-125, 2008.
Keuren et al., "Thrombogenecity of polysaccharide-coated surfaces," Biomaterials, 24:1917-24, 2003.
Kim et al., "Role of the heparin in regulating a transcapillary exchange in far north conditions," Bulletin of the Siberian Branch of the Russian Academy of Medical Sciences, 2(108), 2003.
Kishimoto, S. et al., "Human stem cell factor (SCF) is a heparin-binding cytokine," J. Biochem., 145(3):275-278, 2009.
Kumari, N. et al., "Role of interleukin-6 in cancer progression and therapeutic resistance," Tumour Biol., Sep. 2016, vol. 37(9), pp. 11553-11572 (abstract only).
Larm et al., "A new non-thrombogenic surface prepared by selective covalent binding of heparin via a modified reducing terminal residue," Biomater Med Devices Artif Organs, 11(2&3):161-173, 1983.
Lian, S. et al., "Elevated expression of growth-regulated oncogene-alpha in tumor and stromal cells predicts unfavorable prognosis in pancreatic cancer," Medicine, Jul. 2016, 95(30), pp. 1-8.
Lopatkin et al., "Efferent methods in medicine, M.," Medicine, pp. 266, 272-273, 276-279, 1989.
Low, R. et al., "Protein n, a primosomal DNA replication protein of *Escherichia coli*," Journal of Biological Chemistry, 257(11):6242-6250, 1982.
Mandal, "Sialic acid binding lectins," Experientia 46:433-439, 1990.
Mariano et al, "Tailoring high-cut-off membranes and feasible application in sepsis-associated acute renal failure: in vitro studies," Nephrol Dial Transplant, 20:1116-1126, 2005.
Mattsby-Baltzer, I. et al., "Affinity apheresis for treatment of bacteremia caused by *Staphylococcus aureus* and/or methicilin-resistant *S. aureus* (MRSA)," J. Microbiol. Biotechnol., 21(6):659-664, 2011.
Millen, H. et al., "Glass wool filters for concentrating waterborne viruses and agricultural zoonotic pathogens," J. Vis. Exp., 61:e3930, 2012.
Nadkarni et al., Abstract of "Directional immobilization of heparin onto beaded supports," Anal. Biochem., 222(1):59-67, 1994.
Ofek et al., "Mannose binding and epithelial cell adherence of *Escherichia coli*," Infection and Immunity, 22(1):247-254, 1978.
Park, P. et al., "Activation of Syndecan-1 ectodomain shedding by *Staphylococcus aureus* α-toxin and β-toxin," J. Biol. Chem., 279(1):251-258, 2004.
Popova et al., "Acceleration of epithelial cell syndecan-1 shedding by anthrax hemolytic virulence factors," BMC Microbiolgy, 6:8, pp. 1-16, 2006.
Rauvala, H. et al., "Isolation and some characteristics of an adhesive factor of brain that enhances neurite outgrowth in central neurons," Journal of Biological Chemistry, 262(34):16625-16635, 1987.
Rauvala, H. et al., "The adhesive and neurite-promoting molecule p30: Analysis of the amino-terminal sequence and production of antipeptide antibodies that detect p30 at the surface of neuroblastoma cells and of brain neurons," Journal of Cell Biology, 107(6,1):2293-2305, 1988.
Riesenfeld et al., "Quantitative analysis of N-sulfated, N-acetylated, and unsubstituted glucosamine amino groups in heparin and related polysaccharides," Anal Biochem, 188:383-389, 1990.
Sagnella et al., "Chitosan based surfactant polymers designed to improve blood compatibility on biomaterials," Colloids and Surfaces B: Biointerfaces, 42:147-155, 2005.

Salek-Ardakani, S. et al., "Heparin and heparan sulfate bind interleukin-10 and modulate its activity," Blood, 96:1879-1888, 2000.
Salmivirta, M. et al., "Neurite growth-promoting protein (Amphoterin, p30) binds syndecan," Experimental Cell Research, 200:444-451, 1992.
Sanchez, J. et al., "Control of contact activation on end-point immobilized heparin: The role of antithrombin and the specific antithrombin-binding sequence," J. Bio. Mat. Res., 29:665-661, 1995.
Sasaki et al., Abstract: "Improved method for the immobilization of heparin," J. Chrom., 400:123-32, 1987.
Sato, T. et al., "Experimental study of extracorporeal perfusion for septic shock," Asaio Journal, 39(3):M790-M793, 1993.
Schefold et al., "A novel selective extracorporeal intervention in sepsis: immunoadsorption of endotoxin, interleukin 6, and complement-activating product 5A," Shock, 28(4):418-425, 2007.
Sharon, "Bacterial lectins, cell-cell recognition and infectious disease," FEBS letters, 217(2):145-157, 1987.
Swartz, "Recognition and management of anthrax—an update," New Engl. J. Med., 345(22):1621-1626, 2001.
Thomas et al., "Common oligosaccharide moieties inhibit the adherence of typical and atypical respiratory pathogens," Journal of Microbiology, 53:833-840, 2004.
Utt, M. et al., "Identification of heparan sulphate binding surface proteins of Helicobacter pylori: inhibition of heparan sulphate binding with sulphated carbohydrate polymers," J. Med. Microbiol., 46:541-546, 1997.
Wang, H. et al., "HMG-1 as a late mediator of endotoxin lethality in mice," Science, 285:248-251, 1999.
Ward et al., "Specificity of adsorption in a prototype whole blood affinity therapy device for removal of *Staphylococcus aureus*," Society for Biomaterials 2013 Annual Meeting and Exposition, Apr. 10, 2013, p. 1.
Waugh D. and Wilson, C., "The interleukin-8 pathway in cancer," Clin. Cancer Res., 14(21):6735-41, 2008.
Webb, L. et al., "Binding to heparan sulfate or heparin enhances neutrophil responses to interleukin 8," PNAS USA, 90:7158-62, 1993.
Weber et al., "Development of specific adsorbents for human tumor necrosis factor-α: influence of antibody immobilization on performance and biocompatibility," Biomacromolecules, 6:1864-1870, 2005.
Weir, D., "Carbohydrates as recognition molecules in infection and immunity," FEMS Microbiology Immunology, 47:331-340, 1989.
Wendel et al., "Coating-techniques to improve the hemocompatibility of artificial devices used for extracorporeal circulation," European Journal of Cardio-thoracic Surgery, 16:342-350, 1999.
Yu, J. et al., "Adhesion of coagulase-negative staphylococci and adsorption of plasma proteins to heparinized polymer surfaces," Biomaterials, 15(10):805-814, 1994.
Zhou et al., Abstract: "Heparin-agarose aqueous ethanol suspension," J. Mol. Bio., 271(3):12, 1997.
GE Healthcare, "Size exclusion chromatography columns and resins, Selection guide," 2010, retrieved online at <<https://cdn.gelifesciences.com/dmm3bwsv3/AssetStream.aspx?mediaformatid=10061&destinationid=10016&assetid=13947>> on Jun. 27, 2019, 10 pages.
Brat, D. et al., "The role of interleukin-8 and its receptors in gliomagenesis and tumoral angiogenesis," Neuro-oncology, 7(2):122-133, 2005.
Ghannoum, M. et al., "Extracorporeal treatment for carbamazepine poisoning: Systematic review and recommendations from the EXTRIP workgroup," Clinical Toxicology, 52:993-1004, 2014.
Lemaire, M. et al., "Treatment of paediatric vancomycin intoxication: a case report and review of the literature," NDT Plus, 3:260-264, 2010.

\* cited by examiner

Mixed Media

Heparin-Only

SEMs After Blood Contact

BLOOD FILTRATION SYSTEM CONTAINING MANNOSE COATED SUBSTRATE

CROSS-REFERENCE TO RELATED APPLICATIONS

The present application is a divisional of U.S. patent application Ser. No. 14/973,617, filed Dec. 17, 2015 which is a continuation of PCT/US2014/043358, filed Jun. 20, 2014, which application claims priority to U.S. Provisional Patent Application No. 61/838,854, filed Jun. 24, 2013, the disclosures of which are hereby incorporated by reference in their entireties for all purposes.

BACKGROUND OF THE INVENTION

The emergence of drug-resistant pathogens is a growing threat to the healthcare system. Not only are current antibiotics becoming less effective, large pharmaceutical companies are shifting focus from new antimicrobial development to more lucrative drug discovery programs such as cancer therapeutics. Although it is recognized that "superbugs" are a major concern, the current market for new anti-infective drugs is relatively small in comparison to their significant regulatory and development costs.

The CDC has recently warned of the emergence of carbapenem-resistant Enterobacteriacea (CRE). The mortality rate for CRE bacteremia can be as high as 50%. Resistance of CREs to even the strongest available antibiotics leaves clinicians with few treatment options. The incidence of hospital-acquired CRE infections has increased from just over 1% ten years ago, to 4% today. Although CRE bacteremias are generally nosocomial infections, there is concern that the incidence of community acquired CRE could increase. Currently, the only strategy to combat the spread of CRE infections is through programs that educate healthcare professionals about prevention.

The conventional strategy for combating bacterial infections is to develop active drugs that specifically kill bacteria while avoiding damage to host tissue. This is a major challenge as some of the more potent antibiotics available today are quite toxic. For example, vancomycin is nephrotoxic, and may soon be contraindicated for patients undergoing extracorporeal oxygenation. Even if new antibiotics are successfully developed to address current drug resistance, new superbugs' will still emerge. Clearly, new strategies for combating infection, beyond drug discovery, are required.

Bloodstream infection, or bacteremia, is a major challenge in the ICU. Bacteremia can quickly lead to septic shock, meningitis, endocarditis, osteomyelitis and other metastatic complications. *Staphylococcus aureus, Pseudomonas aeruginosa* and Enterobacteriacea are the most common bacteria responsible for bacteremia or nosocomial infections. Severity of outcome for bacteremic patients is correlated to both the bacterial load and duration of bacteremia. A quantitative rt-PCR study of *E. coli* and *S. aureus* bacteremia patients showed that when the number of rDNA increased over 1238 copies/ml, mortality increased from 14.3% to 42.9% and septic shock increased from 31.4% to 85.7%. (see, "Quantitative rt-PCR Holds Promise as a Screening Tool for Patients with Severe Sepsis." Kirkbright. 2011, Emergence Medicine Australasia, Vol. 23, p. 502). It was also found that a high blood concentration of *N. meningitides* is correlated with prolonged hospitalization, limb or tissue loss, need for dialysis, and mortality. (see, Severity of Meningococcal Disease Associated with Genomic Bacterial Load. Darton. 2009, Clinical Infectious Disease, Vol. 48, pp. 587-84). Likewise, another study showed that the severity of Pneumococcal pneumonia correlated with bacterial load in the blood: the mortality for patients with over 1000 *S. pneumoniae* DNA copies/ml of blood was 25.9% vs. 6.1% for patients exhibiting less than 1000 copies/ml. (see, Rell et al. "Severity of Pneumococcal Pneumonia Associated with Genomic Bacterial Load." 2009, Chest, Vol. 136, pp. 832-840). In yet another study, a follow-up positive blood culture between 48 and 96 hours after initial diagnosis was shown to be the strongest predictor of complicated *S. aureus* bacteremia. Fowler. (see, "Clinical Identifiers of Complicated *Staphylococcus aureus* Bacteremia." 2003, Arch Intern Med, pp. 2066-2072). Compounding the difficulty of effective bacteremia treatment is the often delayed administration of appropriate antibiotic therapy. It had been reported that for each hour of delay in treatment the mortality risk increases over 7%. (see Kumar et al., "Duration of hypotension before initiation of effective antimicrobial therapy is the critical determinant of survival in human septic shock." 6, 2006, Crit Care Med, Vol. 34, pp. 1589-96). A safe, broad-spectrum technology that could quickly reduce the bacterial load, and shorten the duration of bacteremia, would be a major breakthrough, since it could even be used without first identifying the type of bacteria present in the blood.

Although an adsorption hemoperfusion device with only heparinized media is already 'broad-spectrum', with the ability to target many high-profile bacteria responsible for nosocomial infections and bacteremia, gram negative bacteria such as *E. coli, Klebsiella pneumoniae*, and *Pseudomonas aeruginosa* have a comparatively low affinity to heparin/HS.

In view of the foregoing, what is needed in the art are new methods and devices to remove bacteria and pathogens from blood. The present invention satisfies these and other needs.

BRIEF SUMMARY OF THE INVENTION

The present invention provides methods to functionalize the surface of a media with mannose. In certain instances, mannose media and heparinized media can be combined or mixed together to create a single device that targets a very broad spectrum of pathogens. Additionally, close proximity of the mannose media to heparinized media renders the overall device and methods antithrombogenic, thus improving overall safety.

As such, in one embodiment, the present invention comprises a blood-filtration medium comprising, or consisting essentially of, or consisting of:

a. a substrate coated with mannose; and b. optionally, an anti-coagulation component.

In certain embodiments, the substrate comprises non-porous rigid beads, particles, or packing, reticulated foams, a rigid monolithic bed, woven or nonwoven fabric, yarn or solid or hollow dense (not microporous) monofilament fibers, a flat film or barrier membrane, a spiral wound cartridge formed from flat film or dense membrane.

In certain aspects, the mannose is end-point attached to the substrate.

In certain aspects, the anti-coagulation component is present and the component is heparin.

In certain aspects, the substrate comprises substrate coated with heparin.

In certain aspects, the substrate comprises non-porous rigid beads wherein a first portion of the bead is coated with mannose and a second portion of the bead is coated with heparin.

In certain aspects, the mannose and the heparin are each end-point attached to the beads.

In certain aspects, the heparin is heparan sulfate.

In certain aspects, the mannose is D-mannose.

In certain aspects, the mannose is p-aminophenyl-α-D-mannopyranoside.

In certain aspects, the mannose is a polymer of mannose such as mannan.

The present invention also provides a blood filtration cartridge that comprises a container which comprises the medium described above.

The present invention also relates to a system for filtering blood comprising, or consisting essentially of, or consisting of:
  a. a container comprising, or consisting essentially of, or consisting of: a substrate coated with mannose;
  b. optionally, an anti-coagulation component; and
  c. an extracorporeal blood filtration device, wherein the container is functionally coupled to the blood filtration device so that when in use the blood flows through the container and contacts the substrate.

In certain aspects of the system of the invention, the substrate comprises non-porous rigid beads, particles, or packing, reticulated foams, a rigid monolithic bed, woven or non-woven fabric, yarn or solid or hollow dense (not microporous) monofilament fibers, a flat film or barrier membrane, a spiral wound cartridge formed from flat film or dense membrane.

In certain aspects of the system of the invention, the mannose is end-point attached to the substrate.

In certain aspects of the system of the invention, the anti-coagulation component is present and the component is heparin.

In certain aspects of the system of the invention, the substrate comprises substrate coated with heparin.

In certain aspects of the system of the invention, the substrate comprises non-porous rigid beads wherein a first portion of the beads is coated with mannose and a second portion of the bead is coated with heparin.

In certain aspects of the system of the invention, the mannose and the heparin are each end-point attached to the beads.

The present invention also relates to a method for removing at least one gram negative bacteria from blood comprising: contacting a sample of blood with a media discussed above wherein the gram negative bacteria can be an Enterobacteriaceae.

In one embodiment of the method of the invention, the gram negative bacteria is at least one member selected from the group consisting of E. coli, Klebsiella pneumonia, and P. aeruginosa.

In another embodiment, the present invention provides a method for attaching a mannose to an amine containing substrate, the method comprising:
  contacting an aminated substrate with an aqueous solution containing a mannose to form a Schiff base intermediate; and
  contacting the Schiff base with a reducing agent to attach the mannose.

In another embodiment, an appropriate-sized device can be used for pathogen reduction in donated blood.

These and other advantages, objects and embodiments will become more apparent when read with the following figures and detailed description which follow.

DETAILED DESCRIPTION OF THE INVENTION

Figure 1:
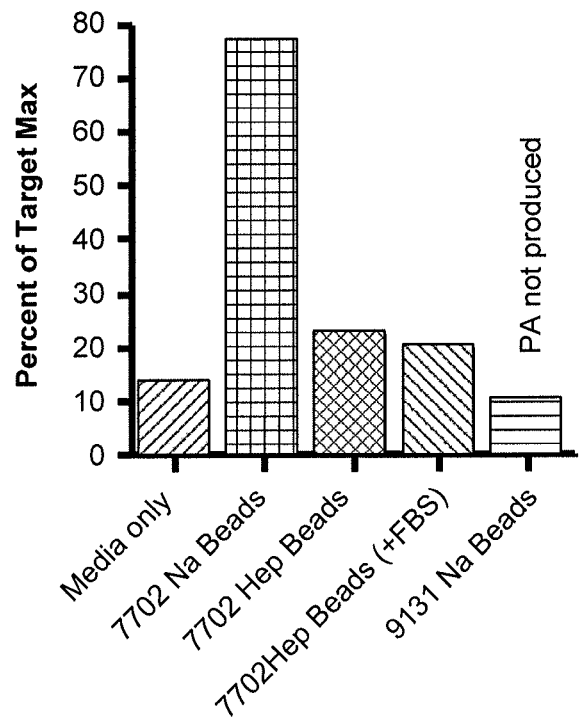
FIG. 1 illustrates one embodiment of the present invention, i.e., protection of macrophages from anthrax protective antigen (PA).

The present invention provides a blood-filtration medium comprising:
  a. a substrate coated with mannose; and
  b. optionally, an anti-coagulation component.

The present invention provides devices and methods that comprise the blood-filtration medium and can remove bacteria and pathogens from mammalian blood. In certain instances, the substrate comprises mannose. In other instances, the anti-coagulation component is present in the medium and the anti-coagulation component is heparin or heparan sulfate. Certain pathogens can be removed from blood using heparin. A mannose functionalized surface can be used to target other bacteria that heparin does not target. Unlike heparin, mannose is not considered antithrombogenic. The spectrum of bacterial removal can be increased by using mannose media alone, or in combination with an anti-coagulation component.

In certain instances, by optimally mixing heparinized adsorption media with mannose media, a blood-safe and broad-spectrum technology is achieved. By combining more than one media/surface chemistry within a single adsorption hemoperfusion device, a very broad spectrum of pathogens is targeted.

One preferred anti-coagulation component is heparin or heparan sulfate. The present invention demonstrates that a high concentration of S. aureus and MRSA can be removed from whole blood using this anti-coagulation component. It is important to note that the drug resistance of MRSA does not affect the binding to the immobilized heparin. Other drug resistant species are also believed to be able to maintain their ability to bind to heparin/heparan sulfate. A list of bacteria that bind to heparin-functional adsorption media of the present invention are shown in Table 1.

TABLE 1

A list of heparan sulfate/heparin binding pathogens and the diseases they cause.

| | |
|---|---|
| S. aureus | Endocarditis, Meningitis, Sepsis |
| MRSA | Flesh Eating Bacteria, Endocarditis, Meningitis, Sepsis |
| Borrelia burgdorferi | Lyme Disease |
| Strep. pyogenes | Scarlet Fever, Strep. Throat, Toxic Shock Syndrome |
| Strep. pneumoniae | Pneumonia, Sepsis, Meningitis, Endocarditis |
| Enterococcus faecalis | Endocarditis, Meningitis, Sepsis |
| Neisseria meningitides | Meningitis, Sepsis |

It has been shown that an extracorporeal device with a high surface area of end-point attached heparin can remove a high concentration of gram positive bacteria (S. aureus and MRSA) from whole blood. (see, Mattsby-Baltzer I. et al., "Affinity Aphaeresis for Treatment of Bacteraemia Caused by *Staphylococcus aureus* and/or Methicillin-resistant *Staphylococcus aureus* (MRSA)." Accepted for Publication March 2011, *Journal for Microbiology and Biotechnology*). In addition, the present application demonstrates using PCR that the bacteria were not killed when they attached to the heparinized surface and therefore did not release potential inflammatory toxins/byproducts into the bloodstream.

The spectra of bacterial removal can be increased by using mannose media alone in the current methods or in combination with an anti-coagulation component. Examples of gram negative bacteria that are not known to have any affinity, or have little affinity for heparin or heparan sulfate, are *E. coli, Klebsiella pneumoniae*, and *P. aeruginosa*. The present methods are able to remove both drug resistant and drug-susceptible Enterobacteriacea using a mannose functionalized media.

Mannose functionalized media includes mannose bound to a substrate. In other instances, mannose media includes p-aminophenyl-α-D-mannopyranoside. In one embodiment, the mannose is bound by end-point attachment to the substrate. In another embodiment, the mannose is attached to the substrate by multi-point attachment.

In other instances, mannose is a polymer of mannose such as mannan. Mannan refers to a plant polysaccharide that is a linear polymer of the sugar mannose. Plant mannans have β(1-4) linkages. Mannan can also refer to a cell wall polysaccharide found in yeasts. This type of mannan has a α(1-6) linked backbone and α(1-2) and α(1-3) linked branches.

Various materials, in shape and composition, can be used as a substrate in the present invention. In certain instances, substrates provide high surface area while promoting the conveyance of adsorbates to the adsorbent sites that bind them (primarily) by forced convective transport. The media is typically provided packed within a container, such as a column, that is designed to hold the media so that it will not be carried away in the flowing blood (e.g., media migration) and permit the flow of blood past essentially all of the media's surface.

Useful substrates for creating the media include, but are not limited to, non-porous rigid beads, particles, or packing, reticulated foams, a rigid monolithic bed (e.g. formed from sintered beads or particles), a column packed with woven or nonwoven fabric, a column packed with a yarn or solid or hollow dense (not microporous) monofilament fibers, a flat film or barrier membrane, a spiral wound cartridge formed from flat film or dense membrane, or a combination of media such as a mixed bead/fabric cartridge.

In certain instances, a suitable substrate is one that is initially microporous, but becomes essentially nonporous when the surface is treated before, during or after the creation of adsorption sites, e.g., via end-point-attached heparin or end-point attached mannose. In one embodiment, the substrate is in the form of solid beads or particles.

Useful beads have a size ranging from about 100 to above 500 microns in diameter such as 100, 200, 300, 400, or 500 microns. The average size of the beads can be from 150 to 450 microns. See for example, WO 2011/068897, the entire contents of which are hereby incorporated by reference. The beads or other high-surface-area substrates may be made from a number of different biocompatible materials, such as natural or synthetic polymers or non-polymeric material including glasses, ceramics and metals, that are essentially free of leachable impurities. Some exemplary polymers including polyurethane, polymethylmethacrylate, polyethylene or co-polymers of ethylene and other monomers, polyethylene imine, polypropylene, and polyisobutylene.

Examples of useful substrates include nonporous Ultra High Molecular Weight Polyethylene (UHMWPE). Other suitable beads are polystyrene, high density and low density polyethylene, silica, polyurethane, and chitosan.

In yet another embodiment, the solid substrate comprises microparticles or hollow fibers. In certain embodiments of the invention, the material of the solid substrate is selected from the group consisting of glass, cellulose, cellulose acetate, chitin, chitosan, crosslinked dextran, crosslinked agarose, polypropylene, polyethylene, polysulfone, polyacrylonitrile, silicone, Teflon® and polyurethanes. In a further embodiment, the carbohydrate is covalently linked to the solid substrate. In a more specific embodiment, the carbohydrate is linked to the solid substrate by covalent end-point attachment.

Covalent attachment of a carbohydrate to a solid substrate provides control of parameters such as surface density and orientation of the immobilized molecules as compared to non-covalent attachment. These parameters have been shown to provide pathogen binding to the immobilized carbohydrate molecules. In certain aspects, the surface concentration of the carbohydrate on the solid substrate is in the range of 0.01 to about 0.2 $\mu g/cm^2$, such as 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19 or 0.2 $\mu g/cm^2$.

In one embodiment, the present media can include both heparin and mannose on a single substrate or may contain a mixture of heparin coated substrates and mannose coated substrates. The coating may be over the entire substrate or a portion of the substrate.

In certain aspects, if the substrate is a bead, the amount of coating on the bead is about 0.4±0.3 mg of mannose and/or heparin per gram of bead. Other amounts include 0.1, 0.2, 0.3, 0.4, 0.5, 0.6, 0.7, 0.8, 0.9 or 1.0±0.3 mg of mannose or heparin per gram of bead. For a bead substrate with surface roughness where the average size is 300 microns, the surface area measured by the BET method is 2700 $cm^2/g$ of beads. The surface coverage of mannose on this bead substrate is then 0.15 $\mu g/cm^2$ of beads, or about 0.01 to about 0.2 $\mu g/cm^2$, or 0.3, 0.4, or 0.5 $\mu g/cm^2$. A suitable range is 0.01 to about 0.5 $\mu g/cm^2$.

If a mixture of both an anti-coagulation component (e.g. heparin) and mannose are included on a single substrate the ratio of heparin:mannose can range from 1:99 to 99:1, and can comprise 1-50% mannose. In one instance, the substrate is coated with 50% mannose, or about 5, 10, 15, 20, 25, 30, 35, 40, 45 or 50% mannose. In one aspect, the substrate is coated with 100% mannose. In other instances, the substrate is coated with 50, 60, 70, 80, 90 or 100% mannose. In one aspect, the combined amount of mannose and heparin coating on a bead is 0.4±0.3 mg total heparin, mannose, or a combination of heparin and mannose per gram of bead.

In certain instances, the substrate is coated with mannose, a mannose derivative or mannose polymer. In other instances, the substrate is a combination of mannose and an anti-coagulation component. In one preferred application of the invention, the substrate is a blend of the different adsorption media and thereafter packed into a cartridge or other housing. This arrangement provides intimate contact among the various surface chemistries on adjacent beads while permitting efficient manufacturing of adsorption cartridges or filters.

One approach is to layer the different media in a parfait-type arrangement within the housing such that the blood contacts the different media in series or parallel flow. One arrangement of the different media within a cartridge is to position unblended anti-coagulation media (anti-thrombogenic) at the entrance and/or the exit of the cartridge, with an optionally blended region containing the mannose interposed between the entrance and exit regions. In the case of media in fiber form, a mixed woven, knitted, or nonwoven structure can be prepared by methods well known in the textile industry to form fabric from the mixed fiber. Alternatively a yarn can be prepared from finer multifilament yarn or monofilament made from two or more fibers with different surface chemistries, as long as one fiber type contains a surface that actively prevents blood clotting on contact. The mixed-fiber yarn can then be used to prepare fabric for blood contact.

In certain aspects of the invention, the immobilized anticoagulation component heparin molecules have a mean molecular weight of more than 10 kDa. In another embodiment of the invention, the immobilized heparin molecules have a mean molecular weight of more than 15 kDa. In yet another embodiment of the invention, the immobilized heparin molecules have a mean molecular weight of more than 21 kDa. In yet another embodiment of the invention, the immobilized heparin molecules have a mean molecular weight of more than 30 kDa. In other embodiments, the immobilized heparin molecules have a mean molecular weight within the range of 15-25 kDa. The mean molecular weight may also be higher, such as in the range of 25-35 kDa. The mean molecular weight can be 1-35 kDa, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 kDa.

In one aspect, the mean molecular weight of the anticoagulation component (e.g., immobilized heparin molecules) in a device or method according to the present invention is significantly higher than the mean molecular weight of the heparin molecules used in the current state of the art. The full length heparin molecules used in accordance with the present invention provide improved binding capacity for heparin binding moieties both in terms of the amount of heparin binding molecules that can be bound per surface area unit of the solid substrate, and in terms of the range of molecules that can be bound by the surface due to the increased selection of binding motifs presented by the immobilized full length heparin molecules.

In certain aspects, mannose and/or heparin are linked to the solid substrate by covalent end-point attachment. Covalent attachment of heparin to a solid substrate provides better control of parameters such as surface density and orientation of the immobilized molecules as compared to non-covalent attachment. The present inventors have found that these parameters are important in order to provide optimal binding of heparin binding harmful agents to the immobilized heparin molecules. In an embodiment, the surface concentration of the heparin and/or mannose on the solid substrate is in the range of 0.001-2.0 µg/cm². In another embodiment, the surface concentration of the heparin on the solid substrate is in the range of 0.005-0.5 µg/cm². Covalent end-point attachment means that the heparin is covalently attached to the solid substrate via the terminal residue of the heparin molecule.

In one embodiment, the solid substrate of the device may preferably comprise a material having a large surface area. The solid substrate of the device may comprise microparticles or hollow fibers, but other types of solid substrates may also be used. The total surface area of the solid substrate may be in the range of 0.1-20 m², preferably in the range of 0.5-3 m², such as 0.5, 1.0, 1.5, 2.0, 2.5 and 3.0 m² and numerical values in-between. In certain embodiments of the invention, the material of the solid substrate is selected from the group consisting of glass, cellulose, cellulose acetate, chitin, chitosan, crosslinked dextran, crosslinked agarose, cross linked alginate, polyethylene, polypropylene, polysulfone, polyacrylonitrile, silicone, fluoropolymers (such as polytetrafluoroethylene) and polyurethanes. The solid substrate may comprise particles or beads. In an embodiment of the inventive device, wherein the solid substrate is particles or beads, the particles or beads may preferably comprise a material selected from the group consisting of polyurethanes, polyolefins, silicones, fluoropolymers (such as polytetrafluoroethylene), poly(methyl methacrylate), glass, cross linked alginates, and cross linked polysaccharides, such as agarose, dextran, cellulose, chitosan and starch. Other materials commonly used in microparticles for medical applications may also be employed. In another embodiment of the invention, the solid substrate comprises a cross linked polysaccharide.

In an embodiment of the inventive device, wherein the solid substrate comprises hollow fibers, the hollow fibers may preferably comprise a material selected from the group consisting of polysulfones, polyamides, polynitriles, polypropylenes, cross linked alginates, and cellulose. Other materials commonly used in hollow fibers for medical applications may also be employed. The hollow fiber may preferably comprise a polysulfone.

The solid substrate of the device may of course also be present in other shapes or forms providing a large surface area.

The size and porosity of the solid substrate should be selected for each application or treatment so as to allow a suitable blood flow rate through the device at an acceptable pressure drop over the device. For certain applications requiring a high blood flow rate and a low pressure drop, a larger diameter particle, pore, hollow fiber or other solid substrate is required. In other applications that do not require a high blood flow rate and a low pressure drop, smaller diameter particles, pores, hollow fibers or other solid substrates may be used. Thus, in an embodiment of the present invention, wherein the solid substrate is present in the form of particles, the particle diameter may be in the range of 10 µm to 5 mm. The particle diameter may also be in the range of 10 µm to 1000 µm such as 200, 300, 400, 500, 600, 700, 800, 900 or 1000 µm.

Generally, a particle size in the range of 20-200 µm such as 10, 20, 30, 40, 50, 60, 70, 80, 90, 100, 110, 120, 130, 140, 150, 160, 170, 180, 190, or 200 µm is useful, but in high flow rate applications larger particles may be required. In certain instances, particles at sizes of 120 µm and below are preferably used with plasma and serum. The solid substrate may comprise one or more hollow fibers. In an embodiment of the present invention, wherein the solid substrate is present in the form of hollow fibers, the inner diameter of the fibers may be in the range of 1 µm to 1000 µm. Generally, an inner diameter in the range of 20-200 µm is useful, but in certain applications larger or smaller diameter fibers may be employed.

The device and methods of the present invention are suitably dimensioned for the blood flow rate required in the application for which it is intended. As non limiting examples, the blood flow rate in extracorporeal circuits for renal dialysis is generally in the range of 200-500 mL/min such as 200, 300, 400, or 500 mL/min, whereas the blood flow rate in extracorporeal circuits for oxygenation is generally in the range of 2000-7000 mL/min such as 2000, 3000, 4000, 5000, 6000, or 7000. In certain applications, such as in extracorporeal circuits for treatment of acute sepsis, the blood flow rate may be much lower, e.g. in the range of 1-100 mL/min.

In operation of the present media, whole blood and/or blood serum from mammals can be used. The amount of blood or blood serum that can be used in the present methods is not intended to be limited. It can range from less than 1 mL to above 1 L, up to and including the entire blood volume of the patient when continuous recirculation back to the patient is employed. One or more 'passes' through the media may be used if needed. The blood may be human or animal blood.

In certain aspects, the methods and device used in some embodiments of the invention can have the following properties: a blood flow in the range of 1-500 ml/min, preferably 5-250 ml/min and low flow resistance.

In addition, the present media can be used in an extracorporeal device. If used extracorporeally, it can comprise a conventional device for extracorporeal treatment of blood and serum from patients. For example, a cartridge or column can then be used in series with conventional extracorporeal circuits such as CPB, hemodialysis, and oxygenation. It can also be used as a shunt or alternative to other filters, so that before or after oxygenation, the blood flow to the oxygenation mechanism is shunted to the present media for removal of endotoxins. The present media can also be used as the sole element in an extracorporeal blood flow circuit.

It has been reported that drug resistant strains of *Klebsiella pneumoniae* expressed a higher concentration of both Type 1 and Type 3 fimbriae. (see, Sahly, J. et al. "Extended-Spectrum B-lactamase Production is Associated with an Increase in Cell Invasion and Expression of Fimbrial Adhesins in *Klebsiella pneumoniae*." 9, 2008, Antimicrobial Agents and Chemotherapy, Vol. 52, pp. 3029-3034). Without being bound to any particular theory it is believed that the drug resistant strains are more virulent because of this simultaneous expression that can lead to higher affinity and attachment to host tissue.

The present invention demonstrates that pathogens will bind to a solid surface or substrate that has been modified with mannose and optionally end-point attached heparin. Table 2 demonstrates the removal of various lab strains of either *S. aureus* or MRSA. For example, in an in vitro blood study (Mattsby-Baltzer I., supra), 85% of MRSA was removed by a single pass through the 'heparin-only' media. The starting concentration of bacteria was $5 \times 10^6$ CFU/mL. In addition to binding MRSA, PCR analysis indicated that the heparinized surface was not bactericidal. This is an important finding that indicates cellular components of (dead) bacteria, which can be inflammatory and toxic to the recipient, are not released into the blood when bacteria attach to the media.

Table 2 shows that *S. aureus* and several strains of MRSA were removed in high yield from whole blood. Depending on the strain, up to 85% of MRSA bacteria were removed by the heparinized substrate.

| *S. Aureus* and MRSA Strains tested | | | | |
|---|---|---|---|---|
| | SA1800T | MRSA485 | MRSA251 | MRSA860 |
| % Removed in one pass | 62% | 85% | 59% | 70% |

To demonstrate capture of viruses, HSV-1 and HSV-2 were removed from human blood, serum, or buffered saline. In this experiment, 1 mL of human blood with $10^{11}$/mL of radiolabeled HSV-1 or HSV-2 virus particles were passed through a column packed with 1 mL of Seraph™ media. It was demonstrated that in this experiment that 99.1% of HSV-1 and 99.8% of HSV-2 were removed from whole blood. (See Table 3 below).

TABLE 3

HSV-1 and HSV-2 reduction using heparinized media Experiments

| Matrix Volume | Virus | Media | Input Challenge | % Reduction |
|---|---|---|---|---|
| 1 mL | Herpes | Buffered NaCl | $10^{11}$ Particles | 94.5 |
| 1 mL | HSV-1 | Human Serum | $10^{11}$ Particles | 97.6 |
| 1 mL | | Human Blood | $10^{11}$ Particles | 99.1 |
| 1 mL | Herpes | Buffered NaCl | $10^{10}$ Particles | 88.3 |
| 1 mL | HSV-2 | Human Blood | $10^{11}$ Particles | 99.8 |

Bacterial toxins have also been shown to bind to heparin-functional media. In another experiment, protective antigen (PA) produced by *B. anthracis* was reduced to background levels and captured before macrophages could be harmed FIG. 1. As shown in the bar graph, the level of cell death reached is 80% when the heparinized media is not used. When heparinized media is added to the experimental setup, macrophage cell death is reduced to 20%, which is the background level of death, indicating the capture of PA before it attacked the macrophages.

A similar study was performed by culturing MRSA to produce α-hemolysin, a pore forming exotoxin. The supernatant from the cultured media was passed over the heparinized media and it was demonstrated that the α-hemolysin was reduced to the background levels of the ELISA analysis.

By optimally mixing anti-coagulation component (e.g., heparinized adsorption media) with the mannose media, a blood-safe and broad-spectrum technology has been developed. As an example, endotoxins are negatively charged, and will not bind to the negatively charged heparin surface. A cationic (positively charged) surface chemistry that targets endotoxins would be extremely thrombogenic if used alone in the absence of heparin. By combining a cationic substrate with the heparinized media on a nano- or micro-scale, the favorable anti-thrombogenic properties of the pure heparinized media can be maintained, while removing high levels of endotoxin from activated human blood. This technique expands the spectrum of adsorbates without compromising the safety of the therapy. Demonstration of this capability is shown in the data provided in FIG. 2.

In certain other aspects, the present invention provides technology for removing pathogens from blood by identifying the natural receptor sites that specific pathogens utilize during their pathogenesis and then developing a biomimetic, high-surface-area extracorporeal affinity adsorption media. The surface chemistry of this developed media then emulates the natural receptor sites resulting in rapid removal of pathogens from whole blood brought in contact with the media, e.g., in an extracorporeal device, used in dialysis-like therapy.

For example, heparan sulfate is a proteoglycan found within syndecans on many different cell surfaces and participates in many biological processes by binding a myriad of proteins, including cytokines and growth factors. The targeting of carbohydrates and proteoglycans for initial attachment is a common mechanism of most pathogens. For instance, influenza viruses will bind to sialic acid, a carbohydrate found in many glycoproteins. To remove these pathogens, sialic acid is employed.

Many gram negative bacteria have mannose binding adhesins located on tips of fimbriae. (see, Sharon, N. "Bacterial lectins, cell-cell recognition and infectious disease." 2, 1987, FEBS letters, Vol. 217, pp. 145-157). Other carbohydrates that have shown to be targeted by bacteria include L-fucose, galactose, and various glucosamines or galactoamines.

There are many different adhesins reported for gram negative bacteria. Most studied are Fimbriae of Type 1, Type 3, Type P, and Type S and also outer membrane protein A (OmpA). Type 1 fimbriae and OmpA have been implicated in the attachment to endothelial cells. Type 1 fimbriae mediate attachment to mannose (mannose-sensitive) and are expressed in the majority of Enterobacteriacea.

Typically, several types of fimbriae are expressed simultaneously. In addition, it has been shown that mannose-sensitive adhesins are present on the bacterial cell surface even when fimbriae are not expressed. Type 1 fimbriae have been shown to interact with human brain microvascular endothelial cells suggesting that fimbriae can be expressed in blood. (see, Teng, C. et al., "*Escherichia coli* K1 RS218 Interacts with Human Brain Microvascular Endothelial Cells via Type 1 Fimbria Bacteria in the Fimbriated State." 5, 2005, Infection and Immunity, Vol. 73, pp. 2923-2931).

The present invention provides methods for removing pathogens from blood by identifying the natural receptor sites that specific pathogens utilize during their pathogenesis and then developing and or designing a biomimetic, high-surface-area extracorporeal affinity adsorption media.

Methods of Attaching to a Substrate

The present invention provides methods of attaching mannose to an amine containing substrate. Mannose, derivatives of mannose and oligomers of mannose are reductively coupled to primary amines on aminated substrates such as aminated beads by reductive amination. Coupling of the open aldehyde form of a reducing mannose to a bead results in a stable secondary amine. Non-reducing mannoses having a reactive amine can be coupled to a bead with an intermediate having an aldehyde functionality.

As such, the present invention provides a method for attaching a mannose to an amine containing substrate, the method comprising:

contacting an aminated substrate with an aqueous solution containing a mannose to form a Schiff base intermediate; and contacting the Schiff base with a reducing agent to attach the mannose.

In certain aspects, the mannose is a reducing sugar. In other aspects, the mannose is a non-reducing sugar (e.g., a mannoside). Suitable mannoses include, but are not limited to, D-mannose, L-mannose, p-aminophenyl-α-D-mannopyranoside, a mannose containing polysaccharide and mannan.

If the mannose is a nonreducing mannose, the method further comprises attaching an intermediate aldehyde (e.g, glutardialdehyde) to the amine substrate prior to the nonreducing mannose.

Typically, the mannose is dissolved in aqueous solution such as an acidic aqueous solution. The mannose aqueous solution is contacted with an aminated substrate such as an aminated bead. A Schiff's base is generated. The Schiff's base is thereafter reduced with a reducing agent. The reducing agent can be for example, sodium cyanoborohydride or sodium borohydride. In certain instances, the method further comprises reacting heparin having a reactive aldehyde functionality.

For heparin attachment, a more reactive aldehyde function in the reducing terminal residue can be achieved by partial, nitrous acid degradation. This shortens the reaction time, but the immobilized heparin will have a lower molecular weight. The coupling is performed in aqueous solution, by reductive amination (cyanoborohydride).

In certain instance, the methods provide a bead having end point attached mannose and heparin.

Covalent end-point attachment means that the carbohydrate is covalently attached to the solid substrate via the terminal residue of the carbohydrate molecule. A second aspect of the present invention provides use of a device comprising a carbohydrate such as mannose immobilized on a solid substrate, the carbohydrate having a binding affinity for a pathogenic microbe, an inflammatory cell or an inflammatory protein, for extracorporeal removal of a pathogenic microbe, inflammatory cell or inflammatory protein from mammalian blood.

In certain aspects, the covalent attachment of full length heparin molecules to a surface is achieved by the reaction of an aldehyde group of the heparin molecule with a primary amino group present on the surface. An inherent property of all carbohydrates is that they have a hemiacetal in their reducing end. This acetal is in equilibrium with the aldehyde form and can form Schiff's bases with primary amines. These Schiff's bases may then be reduced to stable secondary amines. In an embodiment of the inventive device, the heparin is covalently attached to the solid substrate via a stable secondary amino group.

In certain aspects, the present invention relates to a process for the preparation of surfaces carrying end-point attached full length heparin, which method results in full length heparin coated surfaces having a high surface concentration of full length heparin together with mannose. The full length heparin molecules used in the various aspects of the present invention provide a significant increase in the binding capacity for heparin binding entities per surface area unit as compared to the heparin surfaces of the prior art. The heparin is preferably covalently linked to the solid substrate. Covalent coupling of the heparin molecules prevent leaching of heparin into blood in contact with the heparin coated surface.

Leaching of heparin has been a problem in prior art techniques employing for example electrostatic binding of heparin to surfaces.

EXAMPLES

Figure 2:
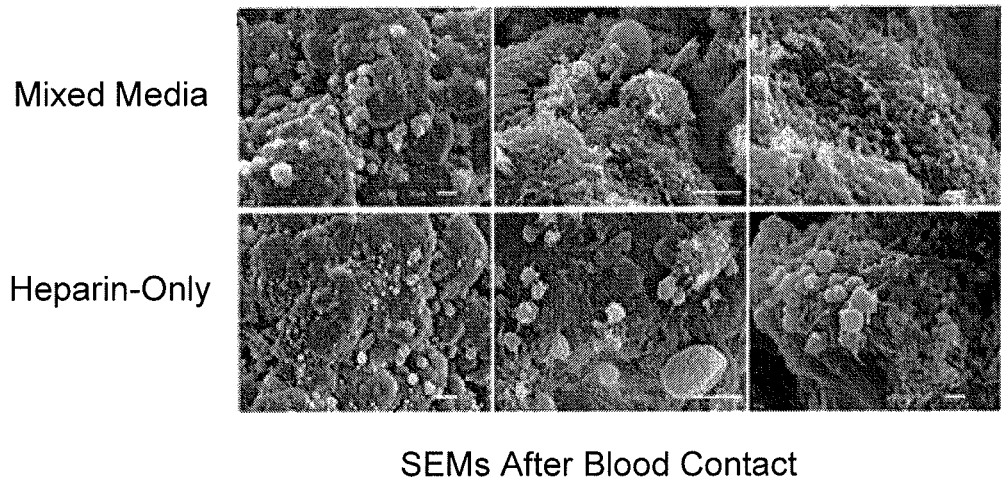
FIG. 2 illustrates SEM micrographs of heparinized and cationic media after passage of whole blood.

In the following experiments, a unit of human blood was incubated with 10 ng/mL of LPS endotoxin and circulated through a control heparinized cartridge (non-LPS binding and antithrombogenic) and a cartridge with a mixture of heparinized beads and cationic media (LPS binding but thrombogenic). The results showed that the heparin-only column did not remove LPS, while the mixed column was unexpectedly efficacious and removed 98% of the endotoxin. There was no evidence of thrombus formation or activated platelets in either cartridge as shown by the SEM micrographs in FIG. 2, nor was there any increase in pressure drop across the adsorption cartridge that would have been caused by thrombus formation.

Example 1—End-Point Attachment of Intact Mannan from *Saccharomyces Cerevisiae* to Aminated Beads Via the Reducing Terminal Residue Oligomers of mannose are reductively coupled to primary amines on aminated beads by reductive amination. Coupling of the open aldehyde form to the bead results in a stable secondary amine and the reaction is as set forth below in Reaction Scheme 1.

In water, the aldehyde function of the D-mannopyranose below is in equilibrium with the α and β forms, formed, by ring closure with the hydroxyl function on carbon atom 5, thus forming a six membered ring. A small proportion of the open free aldehyde form is always present in the equilibrium. The latter react with primary amines and Schiff's bases are formed. By reduction, these bases are irreversible converted to stable secondary amines. Thus, even if the open aldehyde form is less than 1% in the equilibrium the coupling yields are satisfactory.

Reaction Scheme 1

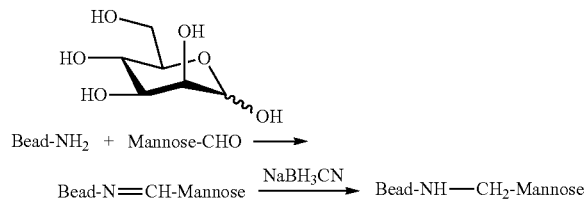

Bead-NH$_2$ + Mannose-CHO ⟶

Bead-N=CH-Mannose $\xrightarrow{\text{NaBH}_3\text{CN}}$ Bead-NH—CH$_2$-Mannose

Mannan from *Saccharomyces cerevisiae* is coupled to primary amines on aminated beads by reductive amination. Coupling of the open aldehyde to the bead results in a stable secondary amine and the reaction is irreversible.

Sodium chloride, 0.73 g. (Sigma-Aldrich, Lot no. BCBG1923V) was dissolved in purified water, 25 mL, with magnetic stirring. Mannan from *Saccharomyces cerevisiae*, 50.0 mg. (Sigma, Lot no. SLBB8777V) was dissolved in the water solution with stirring.

Aminated beads, 10.0 g, (ExThera Medical, Lot no. 1120341) was added to the solution and pH was adjusted to 3.9 with 0.1 M hydrochloric acid. The acid used to create the 0.1 M hydrochloric acid was 2M HCL (ExThera AB, Lot no. 121204) diluted with purified water (1:19).

A solution of sodium cyanoborohydride, 5.0 mg, (Acros Organics, Lot no. A0240008) in 0.5 mL purified water was made. To the bead/mannan mixture was 125 μL of the diluted sodium cyanoborohydride added. The mixture was heated to 80° C. for 8 hours.

The pH was adjusted every two hours to 5.6 and then lowered to 3.9 with 0.1M HCl followed by the addition of 125 μL of Sodium cyanoborohydride solution was added.

The beads were filtered using a glass filter funnel (no. 3) and washed 4 times with 100 mL of DI water. The beads were air-dried during night at room temperature.

Example 2—End-Point Attachment of Low Molecular Weight Oligo-Mannose (LMV-Mannose)

The reaction scheme is essentially as described in Example 1.

Sodium chloride, 0.37 g. (Sigma-Aldrich, Lot no. BCBG1923V) was dissolved in 12.5 ml of DI water with magnetic stirring. LMV-Mannose, 5.0 mg. was dissolved in the water solution also with stirring.

Aminated beads, 5.0 g, (ExThera Medical, Lot no. 1120341) were added to the solution and the pH was adjusted to 3.9 with 0.1 M hydrochloric acid. The acid used to make the 0.1 M hydrochloric acid was 2M HCL (ExThera AB, Lot no. 121204) diluted with purified water (1:19).

A solution of Sodium cyanoborohydride, 5.0 mg, (Acros Organics, Lot no. A0240008) in 0.5 mL purified water was added to the mixture. The mixture was heated to 60° C. for the duration of 24 hours.

The pH was controlled for 1 hour and was subsequently adjusted down to 3.9 with 0.1M HCl from approximately 5.8. After 24 hours pH increased to approx. 5.7. The beads were filtered using a glass filter funnel (no. 3) and washed with 4×50 mL purified water. The beads were air-dried during night at room temperature.

Example 3—End-Point Attachment of Middle Molecular Weight Oligo-Mannose to Aminated Beads Via the Reducing Terminal Residue (MMV-Mannose)

The reaction schemes are essentially the same as described in Example 1.

Oligomers of mannose are reductively coupled to primary amines on aminated beads by reductive amination. Coupling of the open aldehyde form to the bead results in a stable secondary amine and the reaction is irreversible.

The aldehyde function of the monosaccharide unit in the reducing terminal unit is in equilibrium with the hemiacetal, formed by ring closure with the hydroxyl function on carbon atom 5 and, thus forming a six membered ring and the open free aldehyde form. The latter can be used for reductive coupling to primary amines by the use of NaBH$_3$CN.

Sodium chloride, 0.37 g. (Sigma-Aldrich, Lot no. BCBG1923V) was dissolved in 12.5 mL of DI water with magnetic stirring. MMV-Mannose, 5.0 mg. was dissolved in the water solution also with stirring.

Aminated beads, 5.0 g, (ExThera Medical, Lot no. 1120341) were added to the solution and pH was adjusted to 3.9 with 0.1 M hydrochloric acid. The acid used to generate the 0.1 M hydrochloric acid was 2M HCL (ExThera AB, Lot no. 121204) diluted with DI water (1:19).

A solution of Sodium cyanoborohydride, 5.0 mg, (Acros Organics, Lot no. A0240008) in 0.5 mL purified water was added to the mixture. The mixture was heated to 60° C. during 24 hours.

pH was controlled for 1 hour and was subsequently adjusted down to 3.9 with 0.1M HCl from approximately 5.7. After 24 hours pH increased to approximate. 5.6. The beads were filtered using a glass filter funnel (no. 3) and washed with 4×50 mL purified water. The beads were air-dried during night at room temperature.

Example 4—End-Point Attachment of High Molecular Weight Oligo-Mannose to Aminated Beads Via The Reducing Terminal Residue (HMV-Mannose)

The reaction schemes are essentially the same as described in Example 1.

Sodium chloride, 0.37 g. (Sigma-Aldrich, Lot no. BCBG1923V) was dissolved in purified water, 12.5 mL, with magnetic stirring. HMV-Mannose, 5.0 mg., was dissolved in the water solution also with stirring.

Aminated beads, 5.0 g, (ExThera Medical, Lot no. 1120341) were added to the solution and pH was adjusted to 3.9 with 0.1 M hydrochloric acid. The acid used was 2M HCL (ExThera AB, Lot no. 121204) as was diluted with purified water (1:19).

A solution of Sodium cyanoborohydride, 5.0 mg, (Acros Organics, Lot no. A0240008) in 0.5 mL purified water was added to the mixture. The mixture was heated to 60° C. for a period of 24 hours.

pH was controlled for 1 hour and was subsequently adjusted down to 3.9 with 0.1M HCl from approximately 6.4. After 24 hours the pH increased to approx. 6.2. The beads were filtered off on a glass filter funnel (no. 3) and washed with 4×50 mL purified water. The beads were air-dried during night at room temperature.

Example 5—End-Point Attachment of Mannose onto Aminated Aldehyde Activated Beads by Coupling of p-Aminophenyl-α-D-Mannopyranoside Aldehyde activation of aminated PE-beads by using glutardialdehyde proceeds as follows.

Bead-NH$_2$+OCH—CH$_2$—CH$_2$—CH$_2$—CHO→Bead-N═CH—CH$_2$—CH$_2$—CH$_2$—CHO+H$_2$O End-point attachment of p-aminophenyl-α-D-mannopyranoside glutardialdehyde activated beads proceeds as follows:

Bead-N═CH—CH$_2$—CH$_2$—CH$_2$—CHO +

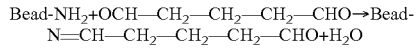

Bead-NH—CH$_2$—CH$_2$—CH$_2$—CH$_2$—CH$_2$—NH-4-Phenyl-α-D-mannopyranoside p-Aminophenyl-α-D-mannopyranoside has been end-point attached to aldehyde activated aminated beads by reductive amination. Sodium chloride, 0.73 g. (Sigma-Aldrich, Lot no. BCBG1923V) was dissolved in purified water, 25 mL. p-aminophenyl-α-D-mannopyranoside, 10.0 mg. was dissolved in the water solution with stirring.

Glutaraldehyde activated beads, 10.0 g, (ExThera AB, Lot no. LAE-I30) were added to the solution and pH was adjusted to 3.9 with 0.1 M hydrochloric acid. The acid used to make the 0.1 M hydrochloric acid was 2M HCL (ExThera AB, Lot no. 121204) diluted with purified water (1:19).

A solution of Sodium cyanoborohydride, 50 mg, (Acros Organics, Lot no. A0240008) in 1 mL purified water was added to the mixture. The mixture was heated to 60° C. for 2 hours.

The pH was controlled for 1 hour and was subsequently adjusted to 3.9 with 0.1M HCl from approximately 6.0. After 2 hours, the pH was 5.9.

The beads were filtered off using a glass filter funnel (no. 3) and washed with 4×100 mL DI water. The beads were air-dried during night at room temperature.

Example 6—End-Point Attachment of Mannose to Chloroacetaldehyde Dimethlacetal Activated Beads Aldehyde activation of aminated PE-beads by using Chloroacetaldehyde dimethylacetal is conducted as follows.

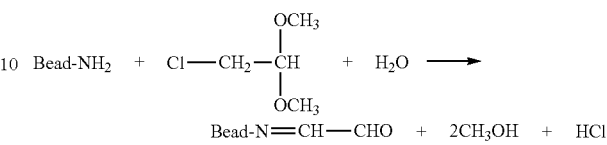

End-point attachment of p-aminophenyl-α-D-mannopyranoside to chloroacetaldehyde dimethylacetal activated beads is conducted as follows.

Bead-N═CH—CHO +

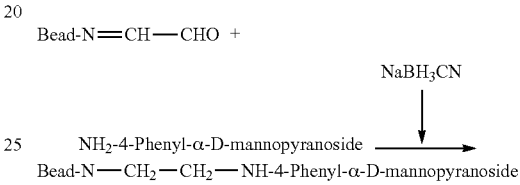

Sodium chloride, 0.73 g. (Sigma-Aldrich, Lot no. BCBG1923V) was dissolved in purified water, 25 mL, with magnetic stirring. p-aminophenyl-α-D-mannopyranoside, 10.0 mg. was dissolved in the water solution while stirring.

Chloroacetaldehyde dimethlacetal activated beads (See report 013-IR p. 6.2), 10.0 g, (ExThera AB, Lot no. LAE-I31) were added to the solution and the pH was adjusted to 3.9 with 0.1 M hydrochloric acid. The acid used the make the 0.1 M hydrochloric acid was 2M HCL (ExThera AB, Lot no. 121204) as was diluted with purified water (1:19).

A solution of Sodium cyanoborohydride, 10 mg, (Acros Organics, Lot no. A0240008) in 1 mL purified water was added to the mixture. The mixture was heated to 60° C. for 2 hours.

The pH was controlled for 1 hour and was subsequently adjusted down to 3.9 with 0.1M HCl from approximately 4.5. After 2 hours pH was approximately 4.5.

The beads were filtered off on a glass filter funnel (no. 3) and washed with 4×100 mL purified water. The beads were air-dried during night at room temperature.

Example 7—Removal of *E. Coli* from Saline Using Mannose Modified Polyethylene Beads Approximately 0.6 grams of mannose and/or heparinized functionalized media was packed into 2.5 ml filter syringes (Mobicol) with 100 micron end plates. 2 ml of bacterial suspensions of *E. coli* ATCC 8739 in saline was prepared by culturing the bacteria overnight and diluting the concentration to 2.05×10$^5$ CFU/mL. The packed filter syringes were rinsed with 3 mL of PBS, followed by passing the bacterial suspension over the syringe three times. Standard dilution and plating techniques were used to enumerate the remaining bacteria after the third passage over the syringe. The test was replicated either two or three times for each

TABLE 4

| Sample # | Starting Concentration E. coli - ATCC 8739 (CFU/ML) | Intact Mannan Modified Polyethylene Beads (0.37 mg/g beads) | | p-Aminophenyl-α-D-mannopyranoside Modified Polyethylene Beads (0.015 mg/g beads) | | End-Point HMW Mannose Modified Polyethylene Beads (0.12 mg/g beads) | | Heparinized Polyethylene Beads | |
|---|---|---|---|---|---|---|---|---|---|
| | | Final Concentration (CFU/mL) | Average % Reduction | Final Concentration (CFU/mL) | Average % Reduction | Final Concentration (CFU/mL) | Average % Reduction | Final Concentration (CFU/mL) | Average % Reduction |
| 1 | 2.05E+05 | 3.50E+04 | 85% | 2.85E+04 | 88% | 2.60E+04 | 86% | 1.47E+05 | 35% |
| 2 | | 3.45E+04 | | 2.50E+04 | | 3.00E+04 | | 1.19E+05 | |
| 3 | | 2.30E+04 | | 2.15E+04 | | NA | | 1.37E+05 | | media. The results are listed below. Heparinized beads were used as a control.

Example 8—Removal of K. Pneumoniae from Saline Using Mannose Modified Polyethylene Beads Approximately 0.6 grams of mannose or heparinized functionalized media was packed into 2.5 ml filter syringes (Mobicol) with 100 micron end plates. 2 ml of bacterial suspensions of K. pneumoniae ATCC 13883 in saline was prepared by culturing the bacteria overnight and diluting the concentration to $2.25 \times 10^5$ CFU/mL. The packed filter syringes were rinsed with 3 mL of PBS, followed by passing the bacterial suspension over the syringe three times. Standard dilution and plating techniques were used to enumerate the remaining bacteria after the third passage over the syringe. The test was replicated either two or three times for each media. The results are listed in Table 5. Heparinized beads were used as a control.

TABLE 5

| Sample # | Starting Concentration K. pneumoniae - ATCC 13883 (CFU/ML) | Intact Mannan Modified Polyethylene Beads (0.37 mg/g beads) | | p-Aminophenyl-ẞ-D-mannopyranoside Modified Polyethylene Beads (0.015 mg/g beads) | | End-Point HMW Mannose Modified Polyethylene Beads (0.12 mg/g beads) | | Heparinized Polyethylene Beads | |
|---|---|---|---|---|---|---|---|---|---|
| | | Final Concentration (CFU/mL) | Average % Reduction | Final Concentration (CFU/mL) | Average % Reduction | Final Concentration (CFU/mL) | Average % Reduction | Final Concentration (CFU/mL) | Average % Reduction |
| 1 | 2.25E+05 | 2.80E+04 | 91% | 1.60E+04 | 92% | 1.05E+04 | 94% | 3.50E+04 | 85% |
| 2 | | 1.85E+04 | | 2.10E+04 | | 1.70E+04 | | 3.45E+04 | |
| 3 | | 1.50E+04 | | 1.40E+04 | | NA | | 2.30E+04 | |

Example 9—Removal of P. Aeruginosa from Saline Using Mannose Modified Polyethylene Beads Approximately 0.6 grams of mannose or heparinized functionalized media was packed into 2.5 ml filter syringes (Mobicol) with 100 micron end plates. 2 ml of bacterial suspensions of P. aeruginosa ATCC 9027 in saline was prepared by culturing the bacteria overnight and diluting the concentration to $3.5 \times 10^5$ CFU/mL. The packed filter syringes were rinsed with 3 mL of PBS, followed by passing the bacterial suspension over the syringe three times. Standard dilution and plating techniques were used to enumerate the remaining bacteria after the third passage over the syringe. The test was replicated either two or three times for each media. The results are shown in Table 6. Heparinized beads were used as a control.

TABLE 6

| Sample # | Starting Concentration P. aeruginosa - ATCC 9027 (CFU/ML) | Intact Mannan Modified Polyethylene Beads (0.37 mg/g beads) | | Heparinized Polyethyelene Beads | |
|---|---|---|---|---|---|
| | | Final Concentration (CFU/mL) | Average % Reduction | Final Concentration (CFU/mL) | Average % Reduction |
| 1 | 3.50E+05 | 6.63E+05 | 84% | 8.75E+04 | 78% |
| 2 | | 4.60E+04 | | 8.95E+04 | |
| 3 | | 5.90E+04 | | 5.70E+04 | |

Example 10—Removal of E. Coli from Blood Using Mannose Modified Polyethylene Beads Approximately 0.6 grams of mannose media was packed into 2.5 ml filter syringes (Mobicol) with 100 micron end plates. 2 ml of bacterial suspensions of E. coli ATCC 8739 in blood was prepared by culturing the bacteria overnight and diluting the concentration to 6.15E+05. The packed filter syringes were rinsed with 3 mL of PBS, followed by passing the bacterial suspension over the syringe three times. Standard dilution and plating techniques were used to enumerate the remaining bacteria after the third passage over the syringe. The test was replicated either two or three times for each media. The results are shown in Table 7.

TABLE 7

| Sample # | Starting Concentration E. coli - ATCC 8739 (CFU/ML) | Intact Mannan Modified Polyethylene Beads (0.37 mg/g beads) | |
|---|---|---|---|
| | | Final Concentration (CFU/mL) | Average % Reduction |
| 1 | 6.15E+05 | 1.62E+03 | 99.75% |
| 2 | | 1.63E+03 | |
| 3 | | 1.37E+03 | |

Example 11—Removal of E. Coli (CRE) from Blood Using Mannose Modified Polyethylene Beads Approximately 0.6 grams of mannose media was packed into 2.5 ml filter syringes (Mobicol) with 100 micron end plates. 2 ml of bacterial suspensions of Carbapenem Resistant Enterobacteriaceae (CRE) E. coli ATCC BAA-2469 in blood was prepared by culturing the bacteria overnight and diluting the concentration to 2.57E+05. The packed filter syringes were rinsed with 3 mL of PBS, followed by passing the bacterial suspension over the syringe three times. Standard dilution and plating techniques were used to enumerate the remaining bacteria after the third passage over the syringe. The test was replicated either two or three times for each media. The results are shown in Table 8.

TABLE 8

| Sample # | Starting Concentration E. coli (CRE) - ATCC BAA-2469 (CFU/ML) | Intact Mannan Modified Polyethylene Beads (0.37 mg/g beads) | |
|---|---|---|---|
| | | Final Concentration (CFU/mL) | Average % Reduction |
| 1 | 2.57E+05 | 1.55E+02 | 99.93% |
| 2 | | 2.15E+02 | |
| 3 | | 2.00E+02 | |

Example 12—Removal of K. Pneumoniae from Blood Using Mannose Modified Polyethylene Beads Approximately 0.6 grams of mannose media was packed into 2.5 ml filter syringes (Mobicol) with 100 micron end plates. 2 ml of bacterial suspensions of K. pneumoniae ATCC 13883 in blood was prepared by culturing the bacteria overnight and diluting the concentration to 4.02E+05. The packed filter syringes were rinsed with 3 mL of PBS, followed by passing the bacterial suspension over the syringe three times. Standard dilution and plating techniques were used to enumerate the remaining bacteria after the third passage over the syringe. The test was replicated either two or three times for each media. The results are shown in Table 9.

TABLE 9

| Sample # | Starting Concentration K. pneumoniae - ATCC 13883 (CFU/ML) | Intact Mannan Modified Polyethylene Beads (0.37 mg/g beads) | |
|---|---|---|---|
| | | Final Concentration (CFU/mL) | Average % Reduction |
| 1 | 4.02E+05 | 2.74E+05 | 33.78% |
| 2 | | 2.37E+05 | |
| 3 | | 2.86E+05 | |

Example 13—Removal of K. Pneumoniae (CRE) from Blood Using Mannose Modified Polyethylene Beads Approximately 0.6 grams of mannose media was packed into 2.5 ml filter syringes (Mobicol) with 100 micron end plates. 2 ml of bacterial suspensions of Carbapenem Resistant Enterobacteriaceae (CRE) K. pneumoniae ATCC BAA-2146 in blood was prepared by culturing the bacteria overnight and diluting the concentration to 1.40E+05. The packed filter syringes were rinsed with 3 mL of PBS, followed by passing the bacterial suspension over the syringe three times. Standard dilution and plating techniques were used to enumerate the remaining bacteria after the third passage over the syringe. The test was replicated either two or three times for each media. The results are shown in Table 10.

TABLE 10

| Sample # | Starting Concentration K. pneumoniae (CRE) - ATCC BAA-2146 (CFU/ML) | Intact Mannan Modified Polyethylene Beads (0.37 mg/g beads) | |
|---|---|---|---|
| | | Final Concentration (CFU/mL) | Average % Reduction |
| 1 | 1.40E+05 | 1.50E+01 | 99.94% |
| 2 | | 1.05E+02 | |
| 3 | | 8.50E+01 | |

Example 14—Removal of K. Pneumoniae (ESBL) from Blood Using Mannose Modified Polyethylene Beads Approximately 0.6 grams of mannose media was packed into 2.5 ml filter syringes (Mobicol) with 100 micron end plates. 2 ml of bacterial suspensions of Extended Spectrum beta-lactamase K. pneumoniae ATCC 700603 in blood was prepared by culturing the bacteria overnight and diluting the concentration to 2.82E+05. The packed filter syringes were rinsed with 3 mL of PBS, followed by passing the bacterial suspension over the syringe three times. Standard dilution and plating techniques were used to enumerate the remaining bacteria after the third passage over the syringe. The test was replicated either two or three times for each media. The results are shown in Table 11.

TABLE 11

| Sample # | Starting Concentration K. pneumoniae (ESBL) - ATCC 700603 (CFU/ML) | Intact Mannan Modified Polyethylene Beads (0.37 mg/g beads) | |
|---|---|---|---|
| | | Final Concentration (CFU/mL) | Average % Reduction |
| 1 | 2.82E+05 | 1.80E+05 | 29.59% |
| 2 | | 2.15E+05 | |
| 3 | | 2.00E+05 | |

Example 15—Removal of S. Pneumoniae from Blood Using Mannose Modified Polyethylene Beads Approximately 0.6 grams of mannose media was packed into 2.5 ml filter syringes (Mobicol) with 100 micron end plates. 2 ml of bacterial suspensions of S. pneumoniae ATCC 6301 in blood was prepared by culturing the bacteria overnight and diluting the concentration to 9.80E+04. The packed filter syringes were rinsed with 3 mL of PBS, followed by passing the bacterial suspension over the syringe three times. Standard dilution and plating techniques were used to enumerate the remaining bacteria after the third passage over the syringe. The test was replicated either two or three times for each media. The results are shown in Table 12.

TABLE 12

| Sample # | Starting Concentration S. pneumoniae- ATCC 6301 (CFU/ML) | Intact Mannan Modified Polyethylene Beads (0.37 mg/g beads) | |
|---|---|---|---|
| | | Final Concentration (CFU/mL) | Average % Reduction |
| 1 | 9.80E+04 | 6.30E+04 | 40.82% |
| 2 | | 5.30E+04 | |

Example 16—Removal of E. Faecalis from Blood Using Mannose Modified Polyethylene Beads Approximately 0.6 grams of mannose media was packed into 2.5 ml filter syringes (Mobicol) with 100 micron end plates. 2 ml of bacterial suspensions of E. faecalis ATCC 29212 in blood was prepared by culturing the bacteria overnight and diluting the concentration to 6.43E+05. The packed filter syringes were rinsed with 3 mL of PBS, followed by passing the bacterial suspension over the syringe three times. Standard dilution and plating techniques were used to enumerate the remaining bacteria after the third passage over the syringe. The test was replicated either two or three times for each media. The results are shown in Table 13.

TABLE 13

| Sample # | Starting Concentration E. faecalis - ATCC 29212 (CFU/ML) | Intact Mannan Modified Polyethylene Beads (0.37 mg/g beads) | |
|---|---|---|---|
| | | Final Concentration (CFU/mL) | Average % Reduction |
| 1 | 6.43E+05 | 6.00E+03 | 99.09% |
| 2 | | 5.00E+03 | |
| 3 | | 6.50E+03 | |

Example 17—Removal of E. Faecalis (VRE) from Blood Using Mannose Modified Polyethylene Beads Approximately 0.6 grams of mannose media was packed into 2.5 ml filter syringes (Mobicol) with 100 micron end plates. 2 ml of bacterial suspensions of Vancomycin Resistant E. faecalis (VRE) ATCC 51575 in blood was prepared by culturing the bacteria overnight and diluting the concentration to 6.17E+05. The packed filter syringes were rinsed with 3 mL of PBS, followed by passing the bacterial suspension over the syringe three times. Standard dilution and plating techniques were used to enumerate the remaining bacteria after the third passage over the syringe. The test was replicated either two or three times for each media. The results are shown in Table 14.

TABLE 14

| Sample # | Starting Concentration E. faecalis (VRE) - ATCC 51575 (CFU/ML) | Intact Mannan Modified Polyethylene Beads (0.37 mg/g beads) | |
|---|---|---|---|
| | | Final Concentration (CFU/mL) | Average % Reduction |
| 1 | 6.17E+05 | 4.25E+04 | 91.22% |
| 2 | | 6.70E+04 | |
| 3 | | 5.30E+04 | |

Example 18—Removal of E. Faecium from Blood Using Mannose Modified Polyethylene Beads Approximately 0.6 grams of mannose media was packed into 2.5 ml filter syringes (Mobicol) with 100 micron end plates. 2 ml of bacterial suspensions of E. faecium ATCC 51559 in blood was prepared by culturing the bacteria overnight and diluting the concentration to 9.17E+05. The packed filter syringes were rinsed with 3 mL of PBS, followed by passing the bacterial suspension over the syringe three times. Standard dilution and plating techniques were used to enumerate the remaining bacteria after the third passage over the syringe. The test was replicated either two or three times for each media. The results are shown in Table 15.

TABLE 15

| Sample # | Starting Concentration E. faecium - ATCC 51559 (CFU/ML) | Intact Mannan Modified Polyethylene Beads (0.37 mg/g beads) | |
|---|---|---|---|
| | | Final Concentration (CFU/mL) | Average % Reduction |
| 1 | 9.17E+05 | 3.50E+05 | 38.18% |
| 2 | | 5.00E+05 | |
| 3 | | 8.50E+05 | |

Example 19—Removal of *A. Baumannii* from Blood Using Mannose Modified Polyethylene Beads Approximately 0.6 grams of mannose media was packed into 2.5 ml filter syringes (Mobicol) with 100 micron end plates. 2 ml of bacterial suspensions of *A. baumannii* ATCC 19606 in blood was prepared by culturing the bacteria overnight and diluting the concentration to 1.83E+05. The packed filter syringes were rinsed with 3 mL of PBS, followed by passing the bacterial suspension over the syringe three times. Standard dilution and plating techniques were used to enumerate the remaining bacteria after the third passage over the syringe. The test was replicated either two or three times for each media. The results are shown in Table 16.

TABLE 16

| Sample # | Starting Concentration A. baumannii - ATCC 19606 (CFU/ML) | Intact Mannan Modified Polyethylene Beads (0.37 mg/g beads) | |
|---|---|---|---|
| | | Final Concentration (CFU/mL) | Average % Reduction |
| 1 | 1.83E+05 | 8.50E+03 | 90.09% |
| 2 | | 5.50E+03 | |
| 3 | | 4.05E+04 | |

The description in this application is intended to be illustrative and not limiting of the invention. One of skill in the art will recognize that variation in materials and methods used in the invention and variation of embodiments of the invention described herein are possible without departing from the invention. It is to be understood that some embodiments of the invention might not exhibit all of the advantages of the invention to achieve every object of the invention. The scope of the invention is defined solely by the claims following.

What is claimed is:

1. A method for attaching a non-reducing mannose to an amine containing substrate, said method comprising:
    providing an amine containing substrate;
    attaching an intermediate aldehyde to the amine containing substrate;
    contacting the amine containing substrate with an aqueous solution containing the non-reducing mannose comprising a reactive amine to form a Schiff base intermediate; and
    contacting the Schiff base with a reducing agent to attach said non-reducing mannose.

2. The method of claim 1, wherein said aqueous solution is acidic.

3. The method of claim 1, wherein said amine containing substrate is an aminated bead.

4. The method of claim 1, wherein said reducing agent is a member selected from sodium cyanoborohydride and sodium borohydride.

5. The method of claim 1, wherein said method further comprises reacting heparin having a reactive aldehyde functionality.

6. A bead having attached the non-reducing mannose made according to the method of claim 1.

7. A bead having the non-reducing attached mannose and heparin made according to the method of claim 5.

8. The method of claim 1, wherein said non-reducing mannose is p-aminophenyl-α-D-mannopyranoside.

9. A method for removing at least one gram negative bacteria from blood comprising:
    contacting a sample of blood with the non-reducing mannose substrate according to claim 1.

10. The method of claim 9, wherein the gram negative bacteria is an Enterobacteriaceae.

11. The method of claim 9, wherein the gram negative bacteria is at least one member selected from the group consisting of *E. coli, Klebsiella pneumoniae*, and *P. aeruginosa*.

12. A non-reducing mannose attached to an amine containing substrate according to claim 1.

* * * * *